US012090145B2

(12) United States Patent
Abdallah et al.

(10) Patent No.: US 12,090,145 B2
(45) Date of Patent: *Sep. 17, 2024

(54) COMBINATION THERAPY FOR TREATING OR PREVENTING DEPRESSION OR OTHER MOOD DISEASES

(71) Applicants: YALE UNIVERSITY, New Haven, CT (US); The United States Government as represented by the Department of Veterans Affairs, Washington, DC (US)

(72) Inventors: Chadi Abdallah, Fairfield, CT (US); John Krystal, Woodbridge, CT (US); Ronald Duman, Guilford, CT (US); Gerard Sanacora, Guilford, CT (US)

(73) Assignees: YALE UNIVERSITY, New Haven, CT (US); The United States Government as represented by the Department of Veterans Affairs, Washington, DC (US)

( * ) Notice: Subject to any disclaimer, the term of this patent is extended or adjusted under 35 U.S.C. 154(b) by 370 days.

This patent is subject to a terminal disclaimer.

(21) Appl. No.: 17/269,470

(22) PCT Filed: Aug. 20, 2019

(86) PCT No.: PCT/US2019/047288
§ 371 (c)(1),
(2) Date: Feb. 18, 2021

(87) PCT Pub. No.: WO2020/041329
PCT Pub. Date: Feb. 27, 2020

(65) Prior Publication Data
US 2021/0251969 A1   Aug. 19, 2021

Related U.S. Application Data

(60) Provisional application No. 62/719,935, filed on Aug. 20, 2018.

(51) Int. Cl.
| | | |
|---|---|---|
| *A61K 31/436* | (2006.01) | |
| *A61K 9/00* | (2006.01) | |
| *A61K 9/08* | (2006.01) | |
| *A61K 31/135* | (2006.01) | |
| *A61K 45/06* | (2006.01) | |
| *A61P 25/24* | (2006.01) | |

(52) U.S. Cl.
CPC .......... *A61K 31/436* (2013.01); *A61K 9/0053* (2013.01); *A61K 9/08* (2013.01); *A61K 31/135* (2013.01); *A61K 45/06* (2013.01); *A61P 25/24* (2018.01)

(58) Field of Classification Search
None
See application file for complete search history.

(56) References Cited

U.S. PATENT DOCUMENTS

| 7,973,043 B2 | 7/2011 | Migaly |
| 2007/0287753 A1 | 12/2007 | Charney et al. |
| 2016/0089377 A1 * | 3/2016 | Karayiorgou ...... A61K 31/4375 546/88 |
| 2020/0085792 A1 * | 3/2020 | Tsai ..................... A61K 9/2018 |

FOREIGN PATENT DOCUMENTS

WO   WO-2011020061 A2 *   2/2011   ........... A61K 31/135

OTHER PUBLICATIONS

Henter, Ioline D., et al., "Mood Therapeutics: Novel Pharmacological Approaches for Treating Depression HHS Public Access", HHS Public Access, Aug. 10, 2017, 1-25.
Yang, Chun , et al., "Mechanistic Target of Rapamycin—Independent Antidepressant Effects of (R)-Ketamine in a Social Defeat Stress Model", Biological Psychiatry, vol. 83, Jan. 1, 2018, 18-28.
Yu, Jing-Jie , et al., "Inhibition of calcineurin in the prefrontal cortex induced depressive-like behavior through mTOR signaling pathway", Psychopharmacology, vol. 225, Aug. 9, 2012, p. 361-372.
International Search Report and Written Opinion, issued on Nov. 19, 2019, in International Patent Application No. PCT/US2019/47288.
Li, Nanxin, et al., "mTOR-Dependent Synapse Formation Underlies the Rapid Antidepressant Effects of NMDA Antagonists", Science, vol. 329, Aug. 20, 2010, pp. 954-964.
Cleary, C. , et al. "Antidepressive-like effects of rapamycin in animal models: Implications formTOR inhibition as a new target for treatment of affective disorders", Brain Research Bulletin 76 (2008), pp. 469-473.
Li, Nanxin, et al., "Glutamate N-methyl-D-aspartate Receptor Antagonists Rapidly Reverse Behavioral and Synaptic Deficits Caused by Chronic Stress Exposure", Biol Psychiatry 2011, vol. 69, pp. 754-761.
Abdallah, Chadi G., et al., "Modulation of the antidepressant effects of ketamine by the mTORC1 inhibitor rapamycin", Neuropsychopharmacology, Feb. 24, 2020, 45:990-997.
Dwyer et al. Biological Psychiatry, 2013, 73(12):1189-1198.
Ignacio et al. British Journal of Clinical Pharmacology, 2016, 82(5):1280-1290.
Office Action (Notice of Allowance and Fees Due (PTOL-85)) dated Aug. 31, 2023 for U.S. Appl. No. 18/049,589 (pp. 1-8).
Office Action (Notice of Allowance and Fees Due (PTOL-85)) dated Sep. 18, 2023 for U.S. Appl. No. 18/049,589 (pp. 1-2).
Andrade, Chittaranjan , "Ketamine for Depression, 1: Clinical Summary of Issues Related to Efficacy, Adverse Effects, and Mechanism of Action", J Clin Psychiatry, 2017 Apr. 2017, e415-e419.
Bains N, A. S. Major Depressive Disorder. [Updated Apr. 10, 2023]. In: StatPearls [Internet]. Treasure Island (FL): StatPearls Publishing; Jan. 2024-. Available from: https://www.ncbi.nlm.nih.gov/books/NBK559078/ (Year: 2024).

(Continued)

*Primary Examiner* — Bong-Sook Baek
(74) *Attorney, Agent, or Firm* — Saul Ewing LLP.; Kathryn Doyle; Domingos J. Silva

(57) ABSTRACT

The present invention provides compositions and methods for treating diseases or disorders using a therapeutically effective amount of a rapid-acting antidepressant (RAAD) and a therapeutically effective amount of a mTOR inhibitor and/or immunosuppressant. In certain embodiments, the RAAD and the mTOR inhibitor and/or immunosuppressant are part of a single pharmaceutical composition.

11 Claims, 1 Drawing Sheet

(56) References Cited

OTHER PUBLICATIONS

Martin-Jurado, O. et al. "Comparison of the effects of racemic ketamine and S-ketamine for anesthesia in Rheem gazelles (Gazella subgutturosa marica) and Subgutturosa gazelles (Gazella subgutturosa subgutturosa)." American journal of veterinary research, 2011. vol. 72, 9: 1164-70. (Year: 2011).

* cited by examiner

COMBINATION THERAPY FOR TREATING OR PREVENTING DEPRESSION OR OTHER MOOD DISEASES

CROSS-REFERENCE TO RELATED APPLICATIONS

The present application is a 35 U.S.C. § 371 national phase application from, and claims priority to, PCT International Patent Application No. PCT/US2019/047288, filed Aug. 20, 2019, which claims priority under 35 U.S.C. § 119(e) to U.S. Provisional Patent Application No. 62/719,935, filed Aug. 20, 2018, all of which are incorporated herein by reference in their entireties.

STATEMENT REGARDING FEDERALLY SPONSORED RESEARCH OR DEVELOPMENT

This invention was made with government support under MH101498 awarded by National Institutes of Health. The government has certain rights in the invention.

BACKGROUND OF THE INVENTION

Major depressive disorder (MDD), also known as depression, is a mental disorder characterized by at least two weeks of continuously low mood, and often accompanied by low self-esteem, loss of interest in previously enjoyable activities, low energy, and unexplained pain. MDD negatively affects a person's social life, sleeping or eating habits, and general health, leading to suicide in about 2-7% of affected adults. Up to 60% of suicide victims had experienced MDD or another mood disorder. MDD patients are often treated with counseling and antidepressants, but unfortunately the efficacy of current pharmacotherapy for depression is only modest.

Traditional antidepressants (AD; e.g., fluoxetine) are used to treat MDD, as well as posttraumatic stress disorders (PTSD), obsessive compulsive disorder (OCD), borderline personality disorder, and several other mood and anxiety disorders. However, these drugs take weeks to months to exert full therapeutic effects, require daily treatment, and approximately 50% of treated patients do not achieve clinical response.

N-methyl-D-aspartate (NMDA) receptor modulators, including ketamine, 4-chlorokynurenine and CERC-301, are under development for the treatment of mood disorders, including MDD and treatment-resistant depression. In fact, ketamine is already employed for this purpose as an off-label therapy in some clinics. Non-limiting examples of NMDA receptor modulators are AP5 (also known as R-2-amino-5-phosphonopentanoate), CERC-301 (also known as MK-0657 or 4-methylbenzyl (3S,4R)-3-fluoro-4-[(2-pyrimidinylamino)methyl]-1-piperidine carboxylate), conantokins, dextromethorphan, dexanabinol, diethyl ether, dizocilpine (also known as MK-801), ketamine, memantine, nitrous oxide, phencyclidine, xenon, methoxetamine, agmatine, and 4-chlorokynurenine (also known as AV-101; this is a prodrug of NMDA receptor antagonist 7-chlorokynurenic acid). Further, the following compounds are known to have weak NMDA receptor antagonism: amantadine, dextropropoxyphene, ethanol, guaifenesin, huperzine A, ibogaine, ketobemidone, methadone, and tramadol. However, the class of NMDA receptor modulators is plagued with high abuse potential, and drug supplies are often misused as recreational drugs. Ketamine (known as K or Special K) is a widely abused substance, especially in southern Asia. Some data suggest that ketamine is the third most commonly abused drug, after methamphetamine and MDMA. Ketamine abuse is associated with damage to the mucosa of the urinary bladder and nasal passages, as well as with cognitive, behavioral, and emotional abnormalities, including persisting psychosis in some heavy users.

NMDA receptor modulators are part of a new class of rapid-acting antidepressants (RAAD; e.g., ketamine, esketamine, rapastinel, dextromethorphan (Nuedexta), scopolamine, mGluR2/3 antagonists, AMPAkine, GlyT1 inhibitor, glycine-site agonists and partial agonists). However, the effects of some of these RAAD last for approximately 7 days, requiring administration 2-3 times per week to maintain the antidepressant effect. In particular, administration of ketamine (often intravenous/intranasal) induces transient psychotomimetic effects and limits the treatment availability to medical settings (by MDs and nurses).

There is thus a need in the art for novel compositions and methods that allow for the administration of NMDA receptor modulators to subjects who can benefit from their pharmacological effects, while minimizing or eliminating abuse liability for these modulators. The present invention addresses and meets this need.

BRIEF SUMMARY OF THE INVENTION

In one aspect, the invention provides a method of treating or preventing a mood disorder in a human subject, wherein the disease or disorder is treatable or preventable by administering a rapid-acting antidepressant (RAAD) to the subject, the method comprising administering to the subject a therapeutically effective amount of the RAAD and a therapeutically effective amount of a mTOR inhibitor and/or immunosuppressant.

In another aspect the invention provides a pharmaceutical composition comprising a RAAD and a mTOR inhibitor and/or immune suppressant, wherein the RAAD and mTOR inhibitor and/or immune suppressant are present in amounts whereby: administration of the pharmaceutical composition to a subject treats in the subject a disease or disorder that is treatable or preventable by the RAAD; and the mTOR inhibitor and/or immune suppressant prolongs at least one biological activity of the RAAD in the subject.

BRIEF DESCRIPTION OF THE DRAWINGS

The following detailed description of illustrative embodiments of the invention will be better understood when read in conjunction with the appended drawings. For the purpose of illustrating the invention, certain illustrative embodiments are shown in the drawings. It should be understood, however, that the invention is not limited to the precise arrangements and instrumentalities of the embodiments shown in the drawings.

FIGS. 1A-1B); Quick Inventory of Depressive Symptomatology scale (QIDS; FIG. 1C); Hamilton Anxiety scale (HAMA; FIG. 1D); ns: $p>0.1$; t: $0.05< p<0.1$; *: $p<0.05$; : $p<0.01$; *: $p<0.001$ (i.e., then number of "*" reflects the number of zeros).

DETAILED DESCRIPTION OF THE INVENTION

Figure 1A:
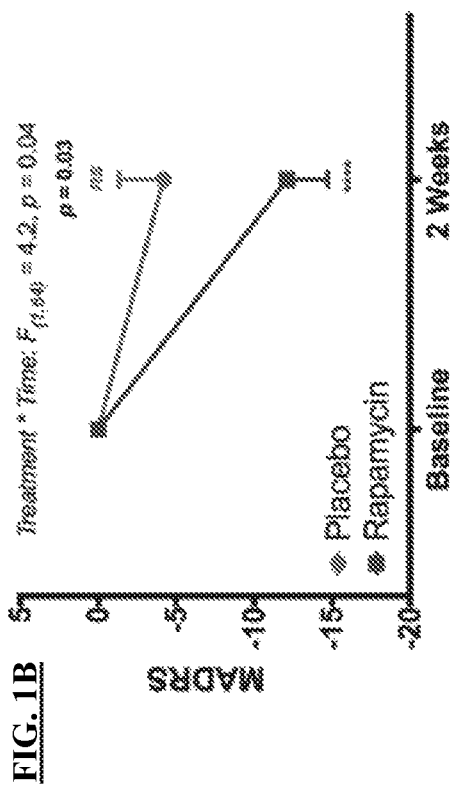
FIGS. 1A-1D comprise a set of graphs illustrating effects of rapamycin on the antidepressant effects of ketamine. Abbreviations: Montgomery-Åsberg Depression Rating Scale (MADRS.

The invention relates in part to the unexpected discovery that a subject in need of treatment for depression can be co-administrated a rapid-acting antidepressant (RAAD; such as but not limited to a NMDA receptor modulator) and a mTOR inhibitor and/or immunosuppressant (e.g., glucocorticoid or calcineurin inhibitor). In certain embodiments, the mTOR inhibitor and/or immunosuppressant prolongs the clinical effect(s) of the RAAD. In other embodiments, the mTOR inhibitor and/or immunosuppressant reduces the abuse liability of the RAAD.

In certain embodiments, the modulator is an antagonist. In other embodiments, the modulator is an inverse agonist. In yet other embodiments, the modulator is a partial antagonist. In yet other embodiments, the modulator is a partial inverse agonist. In yet other embodiments, the modulator is a positive allosteric binder. In yet other embodiments, the modulator is a partial positive allosteric binder. In yet other embodiments, the modulator is a negative allosteric binder. In yet other embodiments, the modulator is a partial negative allosteric binder. In yet other embodiments, the modulator is a functional antagonist. In yet other embodiments, the modulator is a partial functional antagonist.

RAADs are exciting additions to the arsenal available for treating MDD and other mood disorders. However, the effects of some of these RAAD last for a limited amount of time, requiring administration 2-3 times per week to maintain the antidepressant effect during the initiation phase, followed by weekly or monthly dosing for maintenance. Therefore, prolonging the RAAD clinical benefits can reduce the number of drug exposures and thereby enhance cost effectiveness and risk/benefit ratios.

As reported herein, the inventors have shown that administering a single dose of the immunosuppressant rapamycin (also known as sirolimus), which is an inhibitor of the mechanistic target of rapamycin (mTOR), two hours prior to a single ketamine infusion increased the duration of benefits produced by ketamine from a few days to at least two weeks. The combination was safe and very well tolerated. Interestingly, the synergistic effects of ketamine and rapamycin was not observed in non-human animal models of the antidepressant effects of ketamine (Li, et al., 2010, Science 329: 959-964; Li, et al., 2011, Biol. Psychiatry 69:754-761) and thus was not predicted by prior research. Several animal studies suggested that a single rapamycin (mTOR inhibitor) dose blocks the antidepressant effects of ketamine (Li, et al., 2010, Science 329:959-964; Li, et al., 2011, Biol. Psychiatry 69:754-761), while other studies have suggested that repeated rapamycin administration may have antidepressant effects (Cleary, et al., 2008, Brain Res. Bull. 76:469-473).

The invention should not be construed to be limited to rapamycin as the active mTOR inhibitor. In fact, any mTOR inhibitor is useful within the methods of the invention.

The studies presented herein shed light on effects of mTOR inhibition on ketamine antidepressant effects in humans. Contrary to animal studies, where a single dose of rapamycin blocked the antidepressant effects of ketamine, the inventors discovered that rapamycin augments the therapeutic effects of ketamine, maintaining the depression improvement for at least 2 weeks. The two-week boundary was a consequence of the experimental design, and in certain non-limiting embodiments the benefits last longer than about 2 weeks. The co-administration of a mTOR inhibitor with a RAAD allows for extending the clinical benefits of the RAAD, thereby enhancing efficacy and reducing both the risks and costs of treatment for mood and anxiety disorders.

Ketamine treatment is costly and burdensome. The cost of a single ketamine infusion treatment for depression ranges between $600-$2,000 across the U.S. Ketamine is typically administered twice per week for at least the initial four weeks of treatment. Thus, for the first month of treatment, the expected cost would be up to $16,000. Since the combination of ketamine-rapamycin would last a minimum of two weeks, this would be expected to reduce the costs 4-fold, i.e., to about $4,000. In certain embodiments, a formulation comprising a RAAD and a mTOR inhibitor (or immunosuppressant) can be used for intravenous infusion. Reducing the cost and administration burden, while increasing the cost-benefits and safety, of ketamine can substantially increase the number of patients eligible for therapeutic treatment.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, illustrative methods and materials are described. As used herein, each of the following terms has the meaning associated with it in this section.

Generally, the nomenclature used herein and the laboratory procedures in molecular biology, pharmacology and organic chemistry are those well-known and commonly employed in the art.

Standard techniques are used for biochemical and/or biological manipulations. The techniques and procedures are generally performed according to conventional methods in the art and various general references (e.g., Sambrook & Russell, 2012, Molecular Cloning, A Laboratory Approach, Cold Spring Harbor Press, Cold Spring Harbor, N Y, and Ausubel, et al., 2002, Current Protocols in Molecular Biology, John Wiley & Sons, NY), which are provided throughout this document.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity or frequency of at least one sign or symptom of the disease or disorder experienced by a patient is reduced.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" or "therapeutically effective amount" of a compound or composition is that amount of compound or composition that is sufficient to provide a beneficial effect to the subject to which the compound or composition is administered. An "effective amount" of a delivery vehicle is that amount sufficient to effectively bind or deliver a compound or composition.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Naturally occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

As used herein, the term "NMDA" refers to N-methyl-D-aspartate.

As used herein, the term "NMDAR" or "NMDA-R" refers to a NMDA receptor.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or composition useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound or composition useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waves; oils, such as peanut oil, cottonseed oil, safflower oil, sesame oil, olive oil, corn oil and soy bean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound or composition useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" or "therapeutically acceptable salt" refers to a salt of the administered compounds prepared from pharmaceutically acceptable non-toxic acids, including inorganic acids or bases, organic acids or bases, solvates, hydrates, or clathrates thereof.

The terms "pharmaceutically effective amount" and "effective amount" or "therapeutically effective amount" refer to a nontoxic but sufficient amount of an agent to provide the desired biological result. That result can be reduction and/or alleviation of the signs, symptoms, or causes of a disease or disorder, or any other desired alteration of a biological system. The amount of a compound of the invention that constitutes a "therapeutically effective amount" varies depending on the compound, the disease state and its severity, the age of the patient to be treated, and the like. An appropriate effective amount in any individual case may be determined by one of ordinary skill in the art using routine experimentation.

As used herein, the terms "polypeptide," "protein" and "peptide" are used interchangeably and refer to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein. Treatment encompasses prophylaxis and/or therapy. Accordingly the compositions and methods of the present invention are not limited to therapeutic applications and can be used in prophylaxis ones. Thus "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Methods

In one aspect, the present invention provides a method for treating depressive disorders, such as but not limited to MDD, major depressive episode in bipolar disorder (bipolar depression), persistent depressive disorder (dysthymia), disruptive mood dysregulation disorder, major depressive disorder (including major depressive episode), premenstrual dysphoric disorder, substance/medication-induced depressive disorder, depressive disorder due to another medical condition, other specified depressive disorder, unspecified depressive disorder, anxiety disorder, and posttraumatic stress disorder. In certain embodiments, the subject suffering from the depressive disorder further suffers from an addictive disorder (i.e., the subject has comorbid depressive disorder and addictive disorder).

In certain embodiments, the subject in need of such treatment is administered a combination of a RAAD and a mTOR inhibitor and/or immunosuppressant. In other embodiments, the RAAD and the mTOR inhibitor and/or immunosuppressant are co-administered to the subject. In yet other embodiments, the RAAD and the mTOR inhibitor and/or immunosuppressant coformulated. In yet other embodiments, the methods of the invention allow for reducing abuse potential of the RAAD by the subject. In yet other embodiments, the RAAD and the mTOR inhibitor and/or immunosuppressant are the only active agents administered to the subject.

Any RAAD (such as, for example, any NMDA receptor modulator) known in the art is contemplated within the present invention. In certain embodiments, the modulator is an antagonist. In other embodiments, the modulator is an inverse agonist. In yet other embodiments, the modulator is a partial antagonist. In yet other embodiments, the modulator is a partial inverse agonist. In yet other embodiments, the modulator is a positive allosteric binder. In yet other embodiments, the modulator is a partial positive allosteric binder. In yet other embodiments, the modulator is a negative allosteric binder. In yet other embodiments, the modulator is a partial negative allosteric binder. In yet other embodiments, the modulator is a functional antagonist. In yet other embodiments, the modulator is a partial functional antagonist.

Non-limiting examples of RAADs useful within the methods of the invention include:

ketamine (also known as RS-ketamine, R/S-ketamine, or (RS)-2-(2-Chlorophenyl)-2-(methylamino)cyclohexanone);

R-ketamine (also known as (R)-2-(2-Chlorophenyl)-2-(methylamino)cyclohexanone);

S-ketamine (also known as esketamine, or (S)-2-(2-Chlorophenyl)-2-(methylamino) cyclohexanone);

hydroxynorketamine (also known as 2-Amino-2-(2-chlorophenyl)-6-hydroxycyclohexan-1-one);

rapastinel (also known as (S)—N-[(2S,3R)-1-amino-3-hydroxy-1-oxobutan-2-yl]-1-[(S)-1-((2S,3R)-2-amino-3-hydroxy butanoyl)pyrrolidine-2-carbonyl]pyrrolidine-2-carboxamide);

lanicemine (also known as AZD6765, or (1S)-1-phenyl-2-pyridin-2-ylethanamine),

D-cycloserine (also known as 4-amino-3-isoxazolidinone);

scopolamine (also known as hyoscine or (−)-(S)-3-Hydroxy-2-phenylpropionic acid (1R,2R,4S,5S,7a,9S)-9-methyl-3-oxa-9-azatricyclo[3.3.1.0$^{2,4}$]non-7-yl ester);

psilocybin (also known as [3-(2-Dimethylaminoethyl)-1H-indol-4-yl] dihydrogen phosphate);

lysergic acid (also known as LSD or 7-Methyl-4,6,6a,7,8,9-hexahydroindolo[4,3-fg]quinoline-9-carboxylic acid);

ayahuasca or any preparations, fractions, or partially or fully purified fractions thereof;

DMT (also known as 2-(1H-Indol-3-yl)-N,N-dimethylethanamine);

Brexanolone (also known as 1-(3-Hydroxy-10,13-dimethyl-2,3,4,5,6,7,8,9,11,12,14,15,16,17-tetradecahydro-1H-cyclopenta[a]phenanthren-17-yl)ethanone; allopregnanolone; 5α-pregnan-3α-ol-20-one; 3α,5α-tetrahydroprogesterone; or 3α,5α-THP; Sage-547; Sage Therapeutics, Cambridge, MA);

3α-Hydroxy-3β-methyl-21-(4-cyano-1H-pyrazol-1'-yl)-19-nor-5β-pregnan-20-one (also known as 3β-Methyl-21-(4-cyano-1H-pyrazol-1'-yl)-19-norpregnanolone; 3α-Hydroxy-3-methyl-5β-dihydro-21-(4-cyano-1H-pyrazol-1'-yl)-19-norprogesterone; Sage-217; Sage Therapeutics, Cambridge, MA);

(L)-4-Chlorokynurenine (also known as (2S)-2-Amino-4-(2-amino-4-chlorophenyl)-4-oxobutanoic acid or AV-101; VistaGen Therapeutics, South San Francisco, CA);

NV-5138 (Navitor Pharmaceuticals, Cambridge, MA);

D-methadone (also known as (D)-6-(dimethylamino)-4,4-diphenylheptan-3-one);

(1R,2R,3R,5R,6R)-2-amino-3-(3,4-dichlorobenzyloxy)-6-fluorobicyclo[3.1.0]hexane-2,6-dicarboxylic acid (also known as MGS-0039; Taisho Pharmaceutical Co., Saitama, Japan);

midatofel (also known as CPPene, or (R)-4-[(E)-3-phosphonoprop-2-enyl]piperazine-2-carboxylic acid);

selfotel (also known as CGS-19755; or (2S,4R)-4-(phosphonomethyl)piperidine-2-carboxylic acid);

apimostinel (also known as NRX-1074; or (2R)-1-[(2S)-1-[(2S,3R)-2-Amino-3-hydroxy butanoyl] pyrrolidine-2-carbonyl]-N-[(2S,3R)-1-amino-3-hydroxy-1-oxobutan-2-yl]-2-benzylpyrrolidine-2-carboxamide);

basimglurant (also known as RO4917523; or 2-chloro-4-{[1-(4-fluorophenyl)-2,5-dimethyl-1H-imidazol-4-yl]ethynyl}pyridine);

decoglurant (also known as RG1578; or 5-({7-(Trifluoromethyl)-5-[4-(trifluoromethyl)phenyl]pyrazolo[1,5-a]pyrimidin-3-yl}ethynyl)-2-pyridinamine);

tulrampator (also known as CX-1632; S-47445; or 8-cyclopropyl-3-[2-(3-fluorophenyl)ethyl]-7H-[1,3]oxazino[6,5-g][1,2,3]benzotriazine-4,9-dione);

ganaxolone (also known as 1-[(3R,5S,8R,9S,10S,13S,14S,17S)-3-hydroxy-3,10,13-trimethyl-1,2,4,5,6,7,8,9,11,12,14,15,16,17-tetradecahydrocyclopenta[a]phenanthren-17-yl]ethanone);

racemic dextromethorphan (also known as racemic (4bS,8aR,9S)-3-Methoxy-11-methyl-6,7,8,8a,9,10-hexahydro-5H-9,4b-(epiminoethano)phenanthrene);

dextromethorphan;

phencyclidine (also known as 1-(1-phenylcyclohexyl)piperidine);

dizocilpine (also known as MK-801 or (5R,10S)-(+)-5-methyl-10,11-dihydro-5H-dibenzo[a,d]cyclohepten-5,10-imine);

CERC-301 (also known as MK-0657, or 4-Methylbenzyl (3S,4R)-3-fluoro-4-[(2-pyrimidinylamino)methyl]-1-piperidinecarboxylate);

CGP 37849 (also known as (E,2R)-2-amino-4-methyl-5-phosphonopent-3-enoic acid);

1-aminocyclopropanecarboxylic acid;

traxoprodil (also known as CP-101,606, or (1S,2S)-1-(4-hydroxyphenyl)-2-(4-hydroxy-4-phenylpiperidino)-1-propanol);

Ro 25-6981 (also known as (αR,βS)-α-(4-Hydroxyphenyl)-β-methyl-4-(phenylmethyl)-1-piperidinepropanol); and eliprodil (also known as 1-(4-chlorophenyl)-2-[4-[(4-fluorophenyl)methyl]piperidin-1-yl]ethanol);

any salt, solvate, enantiomer, tautomer and geometric isomer thereof, or any mixtures thereof.

In certain embodiments, the RAAD is ketamine, or any salt, solvate, enantiomer, tautomer and geometric isomer thereof. In other embodiments, the RAAD is R-ketamine, or any salt, solvate, enantiomer, tautomer and geometric isomer thereof. In yet other embodiments, the RAAD is S-ketamine, or any salt, solvate, enantiomer, tautomer and geometric isomer thereof. In yet other embodiments, the RAAD is hydroxynorketamine, or any salt, solvate, enantiomer, tautomer and geometric isomer thereof. In yet other embodiments, the RAAD is rapastinel, or any salt, solvate, enantiomer, tautomer and geometric isomer thereof. In yet other embodiments, the RAAD is lanicemine, or any salt, solvate, enantiomer, tautomer and geometric isomer thereof. In yet other embodiments, the RAAD is D-cycloserine, or any salt, solvate, enantiomer, tautomer and geometric isomer thereof. In yet other embodiments, the RAAD is scopolamine, or any salt, solvate, enantiomer, tautomer and geometric isomer thereof. In yet other embodiments, the RAAD is psilocybin, or any salt, solvate, enantiomer, tautomer and geometric isomer thereof. In yet other embodiments, the RAAD is lysergic acid, or any salt, solvate, enantiomer, tautomer and geometric isomer thereof. In yet other embodiments, the RAAD is ayahuasca or any preparations, fractions, or partially or fully purified fractions thereof. In yet other embodiments, the RAAD is DMT, or any salt, solvate, enantiomer, tautomer and geometric isomer thereof. In yet other embodiments, the RAAD is brexanolone, or any salt, solvate, enantiomer, tautomer and geometric isomer thereof. In yet other embodiments, the RAAD is 3α-Hydroxy-3β-methyl-21-(4-cyano-1H-pyrazol-1'-yl)-19-nor-5β-pregnan-20-one, or any salt, solvate, enantiomer, tautomer and geometric isomer thereof. In yet other embodiments, the RAAD is (L)-4-Chlorokynurenine, or any salt, solvate, enantiomer, tautomer and geometric isomer thereof. In yet other embodiments, the RAAD is NV-5138, or any salt, solvate, enantiomer, tautomer and geometric isomer thereof. In yet other embodiments, the RAAD is D-methadone, or any salt, solvate, enantiomer, tautomer and geometric isomer thereof. In yet other embodiments, the RAAD is (1R,2R,3R,5R,6R)-2-amino-3-(3,4-dichlorobenzyloxy)-6-fluorobicyclo[3.1.0]hexane-2,6-dicarboxylic acid, or any salt, solvate, enantiomer, tautomer and geometric isomer thereof. In yet other embodiments, the RAAD is midatofel, or any salt, solvate, enantiomer, tautomer and geometric isomer thereof. In yet other embodiments, the RAAD is selfotel, or any salt, solvate, enantiomer, tautomer and geometric isomer thereof. In yet other embodiments, the RAAD is apimostinel, or any salt, solvate, enantiomer, tautomer and geometric isomer thereof. In yet other embodiments, the RAAD is basimglurant, or any salt, solvate, enantiomer, tautomer and geometric isomer thereof. In yet other embodiments, the RAAD is decoglurant, or any salt, solvate, enantiomer, tautomer and geometric isomer thereof. In yet other embodiments, the RAAD is tulrampator, or any salt, solvate, enantiomer, tautomer and geometric isomer thereof. In yet other embodiments, the RAAD is ganavolone, or any salt, solvate, enantiomer, tautomer and geometric isomer thereof. In yet other embodiments, the RAAD is racemic dextromethorphan, or any salt, solvate, enantiomer, tautomer and geometric isomer thereof. In yet other embodiments, the RAAD is dextromethorphan, or any salt, solvate, enantiomer, tautomer and geometric isomer thereof. In yet other embodiments, the RAAD is phencyclidine, or any salt, solvate, enantiomer, tautomer and geometric isomer thereof. In yet other embodiments, the RAAD is dizocilpine, or any salt, solvate, enantiomer, tautomer and geometric isomer thereof. In yet other embodiments, the RAAD is CERC-301, or any salt, solvate, enantiomer, tautomer and geometric isomer thereof. In yet other embodiments, the RAAD is CGP 37849, or any salt, solvate, enantiomer, tautomer and geometric isomer thereof. In yet other embodiments, the RAAD is 1-aminocyclopropanecarboxylic acid, or any salt, solvate, enantiomer, tautomer and geometric isomer thereof. In yet other embodiments, the RAAD is traxoprodil, or any salt, solvate, enantiomer, tautomer and geometric isomer thereof. In yet other embodiments, the RAAD is Ro 25-6981, or any salt, solvate, enantiomer, tautomer and geometric isomer thereof. In yet other embodiments, the RAAD is eliprodil, or any salt, solvate, enantiomer, tautomer and geometric isomer thereof.

In certain embodiments, the RAAD is not ketamine, or any salt, solvate, enantiomer, tautomer and geometric isomer thereof. In other embodiments, the RAAD is not R-ketamine, or any salt, solvate, enantiomer, tautomer and geometric isomer thereof. In yet other embodiments, the RAAD is not S-ketamine, or any salt, solvate, enantiomer, tautomer and geometric isomer thereof. In yet other embodiments, the RAAD is not hydroxynorketamine, or any salt, solvate, enantiomer, tautomer and geometric isomer thereof. In yet other embodiments, the RAAD is not rapastinel, or any salt, solvate, enantiomer, tautomer and geometric isomer thereof. In yet other embodiments, the RAAD is not lanicemine, or any salt, solvate, enantiomer, tautomer and geometric isomer thereof. In yet other embodiments, the RAAD is not D-cycloserine, or any salt, solvate, enantiomer, tautomer and geometric isomer thereof. In yet other embodiments, the RAAD is not scopolamine, or any salt, solvate, enantiomer, tautomer and geometric isomer thereof. In yet other embodiments, the RAAD is not psilocybin, or any salt, solvate, enantiomer, tautomer and geometric isomer thereof. In yet other embodiments, the RAAD is not lysergic acid, or any salt, solvate, enantiomer, tautomer and geometric isomer thereof. In yet other embodiments, the RAAD is not ayahuasca or any preparations, fractions, or partially or fully purified fractions thereof. In yet other embodiments, the RAAD is not DMT, or any salt, solvate, enantiomer, tautomer and geometric isomer thereof. In yet other embodiments, the RAAD is not brexanolone, or any salt, solvate, enantiomer, tautomer and geometric isomer thereof. In yet other embodiments, the RAAD is not 3α-Hydroxy-3β-methyl-21-(4-cyano-1H-pyrazol-1'-yl)-19-nor-5β-pregnan-20-one, or any salt, solvate, enantiomer, tautomer and geometric isomer thereof. In yet other embodiments, the RAAD is not (L)-4-Chlorokynurenine, or any salt, solvate, enantiomer, tautomer and geometric isomer thereof. In yet other embodiments, the RAAD is not NV-5138, or any salt, solvate, enantiomer, tautomer and geometric isomer thereof. In yet other embodiments, the RAAD is not D-methadone, or any salt, solvate, enantiomer, tautomer and geometric isomer thereof. In yet other embodiments, the RAAD is not (1R,2R,3R,5R,6R)-2-amino-3-(3,4-dichlorobenzyloxy)-6-fluorobicyclo[3.1.0]hexane-2,6-dicarboxylic acid, or any salt, solvate, enantiomer, tautomer and geometric isomer thereof. In yet other embodiments, the RAAD is not midatofel, or any salt, solvate, enantiomer, tautomer and geometric isomer thereof. In yet other embodiments, the RAAD is not selfotel, or any salt, solvate, enantiomer, tautomer and geometric isomer thereof. In yet other embodiments, the RAAD is not apimostinel, or any salt, solvate, enantiomer, tautomer and geometric isomer thereof. In yet other embodiments, the RAAD is not basimglurant, or any salt, solvate, enantiomer, tautomer and geometric isomer thereof. In yet other embodiments, the RAAD is not decoglurant, or any salt, solvate, enantiomer, tautomer and geometric isomer thereof. In yet other embodiments, the RAAD is not tulrampator, or any salt, solvate, enantiomer, tautomer and geometric isomer thereof. In yet other embodiments, the RAAD is not ganavolone, or any salt, solvate, enantiomer, tautomer and geometric isomer thereof. In yet other embodiments, the RAAD is not racemic dextromethorphan, or any salt, solvate, enantiomer, tautomer and geometric isomer thereof. In yet other embodiments, the RAAD is not dextromethorphan, or any salt, solvate, enantiomer, tautomer and geometric isomer thereof. In yet other embodiments, the RAAD is not phencyclidine, or any salt, solvate, enantiomer, tautomer and geometric isomer thereof. In yet other embodiments, the RAAD is not dizocilpine, or any salt, solvate, enantiomer, tautomer and geometric isomer thereof. In yet other embodiments, the RAAD is not CERC-301, or any salt, solvate, enantiomer, tautomer and geometric isomer thereof. In yet other embodiments, the RAAD is not CGP 37849, or any salt, solvate, enantiomer, tautomer and geometric isomer thereof. In yet other embodiments, the RAAD is not 1-aminocyclopropanecarboxylic acid, or any salt, solvate, enantiomer, tautomer and geometric isomer thereof. In yet other embodiments, the RAAD is not traxoprodil, or any salt, solvate, enantiomer, tautomer and geometric isomer thereof. In yet other embodiments, the RAAD is not Ro 25-6981, or any salt, solvate, enantiomer, tautomer and geometric isomer thereof. In yet other embodiments, the RAAD is not eliprodil, or any salt, solvate, enantiomer, tautomer and geometric isomer thereof.

In certain embodiments, the mTOR inhibitor is BEZ235, or a salt, solvate, enantiomer or diastereoisomer thereof. In certain embodiments, the mTOR inhibitor is rapamycin, or a salt, solvate, enantiomer or diastereoisomer thereof. In certain embodiments, the mTOR inhibitor is everolimus, or a salt, solvate, enantiomer or diastereoisomer thereof. In certain embodiments, the mTOR inhibitor is AZD8055, or a salt, solvate, enantiomer or diastereoisomer thereof. In certain embodiments, the mTOR inhibitor is Temsirolimus, or a salt, solvate, enantiomer or diastereoisomer thereof. In certain embodiments, the mTOR inhibitor is KU-0063794, or a salt, solvate, enantiomer or diastereoisomer thereof. In certain embodiments, the mTOR inhibitor is PI-103, or a salt, solvate, enantiomer or diastereoisomer thereof. In certain embodiments, the mTOR inhibitor is Torkinib, or a salt, solvate, enantiomer or diastereoisomer thereof. In certain embodiments, the mTOR inhibitor is Tacrolimus, or a salt, solvate, enantiomer or diastereoisomer thereof. In certain embodiments, the mTOR inhibitor is Ridaforolimus, or a salt, solvate, enantiomer or diastereoisomer thereof. In certain embodiments, the mTOR inhibitor is INK-128, or a salt, solvate, enantiomer or diastereoisomer thereof. In certain embodiments, the mTOR inhibitor is Voxtalisib, or a salt, solvate, enantiomer or diastereoisomer thereof. In certain embodiments, the mTOR inhibitor is Torin-1, or a salt, solvate, enantiomer or diastereoisomer thereof. In certain embodiments, the mTOR inhibitor is Omipalisib, or a salt, solvate, enantiomer or diastereoisomer thereof. In certain embodiments, the mTOR inhibitor is OSI-027, or a salt, solvate, enantiomer or diastereoisomer thereof. In certain embodiments, the mTOR inhibitor is PF-04691502, or a salt, solvate, enantiomer or diastereoisomer thereof. In certain embodiments, the mTOR inhibitor is Apitolisib, or a salt, solvate, enantiomer or diastereoisomer thereof. In certain embodiments, the mTOR inhibitor is GSK1059615, or a salt, solvate, enantiomer or diastereoisomer thereof. In certain embodiments, the mTOR inhibitor is WYE-354, or a salt, solvate, enantiomer or diastereoisomer thereof. In certain embodiments, the mTOR inhibitor is Gedatolisib, or a salt, solvate, enantiomer or diastereoisomer thereof. In certain embodiments, the mTOR inhibitor is AZD-2014, or a salt, solvate, enantiomer or diastereoisomer thereof. In certain embodiments, the mTOR inhibitor is Torin-2, or a salt, solvate, enantiomer or diastereoisomer thereof. In certain embodiments, the mTOR inhibitor is WYE-125132, or a salt, solvate, enantiomer or diastereoisomer thereof. In certain embodiments, the mTOR inhibitor is BGT226, or a salt, solvate, enantiomer or diastereoisomer thereof. In certain embodiments, the mTOR inhibitor is Palomid-529, or a salt, solvate, enantiomer or diastereoisomer thereof. In certain embodiments, the mTOR inhibitor is PP121, or a salt, solvate, enantiomer or diastereoisomer thereof. In certain embodiments, the mTOR inhibitor is WYE-687, or a salt, solvate, enantiomer or diastereoisomer thereof. In certain embodiments, the mTOR inhibitor is CH5132799, or a salt, solvate, enantiomer or diastereoisomer thereof. In certain embodiments, the mTOR inhibitor is Way-600, or a salt, solvate, enantiomer or diastereoisomer thereof. In certain embodiments, the mTOR inhibitor is ETP-46464, or a salt, solvate, enantiomer or diastereoisomer thereof. In certain embodiments, the mTOR inhibitor is GDC-0349, or a salt, solvate, enantiomer or diastereoisomer thereof. In certain embodiments, the mTOR inhibitor is XL388, or a salt, solvate, enantiomer or diastereoisomer thereof. In certain embodiments, the mTOR inhibitor is Zotarolimus, or a salt, solvate, enantiomer or diastereoisomer thereof. In other embodiments, the mTOR inhibitor is at least one selected from the group consisting of rapamycin, Ridaforolimus, and Everolimus, or a salt, solvate, enantiomer or diastereoisomer thereof. In yet other embodiments, the mTOR inhibitor is rapamycin, or a salt, solvate, enantiomer or diastereoisomer thereof.

In certain embodiments, the mTOR inhibitor is not BEZ235, or a salt, solvate, enantiomer or diastereoisomer thereof. In certain embodiments, the mTOR inhibitor is not rapamycin, or a salt, solvate, enantiomer or diastereoisomer thereof. In certain embodiments, the mTOR inhibitor is not everolimus, or a salt, solvate, enantiomer or diastereoisomer thereof. In certain embodiments, the mTOR inhibitor is not AZD8055, or a salt, solvate, enantiomer or diastereoisomer thereof. In certain embodiments, the mTOR inhibitor is not Temsirolimus, or a salt, solvate, enantiomer or diastereoisomer thereof. In certain embodiments, the mTOR inhibitor is not KU-0063794, or a salt, solvate, enantiomer or diastereoisomer thereof. In certain embodiments, the mTOR inhibitor is not PI-103, or a salt, solvate, enantiomer or diastereoisomer thereof. In certain embodiments, the mTOR inhibitor is not Torkinib, or a salt, solvate, enantiomer or diastereoisomer thereof. In certain embodiments, the mTOR inhibitor is not Tacrolimus, or a salt, solvate, enantiomer or diastereoisomer thereof. In certain embodiments, the mTOR inhibitor is not Ridaforolimus, or a salt, solvate, enantiomer or diastereoisomer thereof. In certain embodiments, the mTOR inhibitor is not INK-128, or a salt, solvate, enantiomer or diastereoisomer thereof. In certain embodiments, the mTOR inhibitor is not Voxtalisib, or a salt, solvate, enantiomer or diastereoisomer thereof. In certain embodiments, the mTOR inhibitor is not Torin-1, or a salt, solvate, enantiomer or diastereoisomer thereof. In certain embodiments, the mTOR inhibitor is not Omipalisib, or a salt, solvate, enantiomer or diastereoisomer thereof. In certain embodiments, the mTOR inhibitor is not OSI-027, or a salt, solvate, enantiomer or diastereoisomer thereof. In certain embodiments, the mTOR inhibitor is not PF-04691502, or a salt, solvate, enantiomer or diastereoisomer thereof. In certain embodiments, the mTOR inhibitor is not Apitolisib, or a salt, solvate, enantiomer or diastereoisomer thereof. In certain embodiments, the mTOR inhibitor is not GSK1059615, or a salt, solvate, enantiomer or diastereoisomer thereof. In certain embodiments, the mTOR inhibitor is not WYE-354, or a salt, solvate, enantiomer or diastereoisomer thereof. In certain embodiments, the mTOR inhibitor is not Gedatolisib, or a salt, solvate, enantiomer or diastereoisomer thereof. In certain embodiments, the mTOR inhibitor is not AZD-2014, or a salt, solvate, enantiomer or diastereoisomer thereof. In certain embodiments, the mTOR inhibitor is not Torin-2, or a salt, solvate, enantiomer or diastereoisomer thereof. In certain embodiments, the mTOR inhibitor is not WYE-125132, or a salt, solvate, enantiomer or diastereoisomer thereof. In certain embodiments, the mTOR inhibitor is not BGT226, or a salt, solvate, enantiomer or diastereoisomer thereof. In certain embodiments, the mTOR inhibitor is not Palomid-529, or a salt, solvate, enantiomer or diastereoisomer thereof. In certain embodiments, the mTOR inhibitor is not PP121, or a salt, solvate, enantiomer or diastereoisomer thereof. In certain embodiments, the mTOR inhibitor is not WYE-687, or a salt, solvate, enantiomer or diastereoisomer thereof. In certain embodiments, the mTOR inhibitor is not CH5132799, or a salt, solvate, enantiomer or diastereoisomer thereof. In certain embodiments, the mTOR inhibitor is not Way-600, or a salt, solvate, enantiomer or diastereoisomer thereof. In certain embodiments, the mTOR inhibitor is not ETP-46464, or a salt, solvate, enantiomer or diastereoisomer thereof. In certain embodiments, the mTOR inhibitor is not GDC-0349, or a salt, solvate, enantiomer or diastereoisomer thereof. In certain embodiments, the mTOR inhibitor is not XL388, or a salt, solvate, enantiomer or diastereoisomer thereof. In certain embodiments, the mTOR inhibitor is not Zotarolimus, or a salt, solvate, enantiomer or diastereoisomer thereof.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

Salts

The compounds described herein can form salts with acids and/or bases, and such salts are included in the present invention. In certain embodiments, the salts are pharmaceutically acceptable salts. The term "salts" embraces addition salts of free acids and/or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxy butyric, salicylic, galactaric and galacturonic acid.

Suitable pharmaceutically acceptable base addition salts of compounds of the invention include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (also known as N-methylglucamine) and procaine. All of these salts may be prepared from the corresponding compound by reacting, for example, the appropriate acid or base with the compound.

Compositions

The present invention includes pharmaceutical compositions comprising at least one pharmaceutically acceptable carrier and one or more pharmaceutically active agents contemplated herein. The pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit.

In certain embodiments, the RAAD and the mTOR inhibitor and/or immunosuppressant are coformulated in a pharmaceutical composition. In other embodiments, the RAAD and the mTOR inhibitor and/or immunosuppressant are coformulated in a way whereby physical separation of the RAAD and the mTOR inhibitor and/or immunosuppressant is not possible and/or feasible. In yet other embodiments, separation of the RAAD and the mTOR inhibitor and/or immunosuppressant requires chemical purification (using extractive procedures, chromatographic separation and the like). In yet other embodiments, separation of the RAAD and the mTOR inhibitor and/or immunosuppressant requires denaturation and/or destruction of the pharmaceutical composition.

In certain embodiments, the pharmaceutical compositions of the invention comprise a RAAD and a mTOR inhibitor and/or immunosuppressant, wherein the RAAD and the mTOR inhibitor and/or immunosuppressant are present in amounts whereby: administration of the pharmaceutical compositions to a subject treats in the subject a disease or disorder that is treatable or preventable by RAAD; and the mTOR inhibitor and/or immunosuppressant prolong at least one biological effect of the RAAD in the subject.

In certain embodiments, the pharmaceutical compositions of the invention, or any of the active agents contemplated in the invention (separately and/or in combination), are administered to the subject in need thereof using any known and applicable route of administration, such as for example, (intra)nasal, inhalational, topical, oral, buccal, rectal, pleural, peritoneal, vaginal, intramuscular, subcutaneous, transdermal, epidural, intratracheal, otic, intraocular, intrathecal, and intravenous. In certain embodiments, the pharmaceutical compositions of the invention, or any of the active agents contemplated in the invention (separately and/or in combination), are administered to the subject in need thereof (intra)nasally. In yet other embodiments, the pharmaceutical compositions of the invention, or any of the active agents contemplated in the invention (separately and/or in combination), are administered to the subject using a transdermal patch.

Contemplated modes of administration of compounds and/or compositions useful within the invention, including (intra)nasal delivery, are recited in the following applications, which are incorporated herein in their entireties by reference: US20040059003, US20040138298, US20040166067, US20070287753, US20080041367, US20080153879, US20120270903, US20120277267, US20140171514, US20140256821, US20140274981, US20140275276, US20140275277, US20140275278, US20150056308, US20150196501, US20150283123, US20160000733, US20160175266, EP1103256, and DE102007009888.

In certain embodiments, the dose of the RAAD (such as, but not limited to, ketamine, R-ketamine, S-ketamine, or any mixtures thereof) administered (intra)nasally, intravenously, intramuscularly and/or orally to the subject ranges from about 0.15 mg/kg to about 10 mg/kg. For example, the dose of RAAD administered (intra)nasally, intravenously, intramuscularly and/or orally to the subject is selected from the group consisting of about 0.15 mg/kg. 0.2 mg/kg, 0.25 mg/kg, 0.5 mg/kg, 0.75 mg/kg, 1 mg/kg, 1.5 mg/kg, 2 mg/kg, 2.5 mg/kg, 3 mg/kg. 3.5 mg/kg. 4 mg/kg. 4.5 mg/kg, 5 mg/kg, 5.5 mg/kg, 6 mg/kg, 6.5 mg/kg, 7 mg/kg, 7.5 mg/kg. 8 mg/kg. 8.5 mg/kg, 9 mg/kg, 9.5 mg/kg. 10 mg/kg, and any fraction or multiple thereof.

In certain embodiments, the amount of RAAD (such as, but not limited to, ketamine, R-ketamine, S-ketamine, or any mixtures thereof) administered (intra)nasally, intravenously, intramuscularly and/or orally to the subject ranges from about 1 mg to about 200 mg. For example, the amount of RAAD administered (intra)nasally, intravenously, intramuscularly and/or orally to the subject is selected from the group consisting of about 1 mg. 2 mg. 3 mg, 4 mg. 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 110 mg, 120 mg, 130 mg. 140 mg. 150 mg. 160 mg, 170 mg, 180 mg, 190 mg. 200 mg, and any fraction or multiple thereof.

In certain embodiments, the dose of mTOR inhibitor and/or immunosuppressant (such as, but not limited to, rapamycin) administered (intra)nasally, intravenously, intramuscularly and/or orally to the subject ranges from about 0.5 mg to about 40 mg. For example, the dose of mTOR inhibitor administered intravenously to the subject is selected from the group consisting of about 0.5 mg, 1 mg, 2 mg, 3 mg, 4 mg, 5 mg, 6 mg, 7 mg, 8 mg, 9 mg, 10 mg, 15 mg, 20 mg, 30 mg, 40 mg, and any fraction or multiple thereof.

Methods

The invention provides a method of treating or preventing a disease in a subject, wherein the disease or disorder is treatable or preventable by administering a RAAD (such as, but not limited to, a N-methyl-D-aspartate (NMDA) receptor modulator) to the subject.

The invention further provides a method of preventing and/or minimizing abuse of a RAAD (such as, but not limited to, a NMDA receptor modulator) by a subject.

The invention further provides a method of treating or preventing major depressive disorder in a subject.

In certain embodiments, the method comprises administering to the subject a therapeutically effective amount of the RAAD and a therapeutically effective amount of a mTOR inhibitor and/or immunosuppressant.

In certain embodiments, the RAAD and mTOR inhibitor and/or immunosuppressant are co-administered to the subject. In other embodiments, the RAAD and mTOR inhibitor and/or immunosuppressant are co-formulated as a pharmaceutical composition.

In certain embodiments, the mTOR inhibitor and/or immunosuppressant is administered to the subject at least once before the RAAD is administered to the subject. In other embodiments, the mTOR inhibitor and/or immunosuppressant is administered to the subject at least about 0.5 hours, about 1 hour, about 2 hours, or about 3 hours before the RAAD is administered to the subject In certain embodiments, the RAAD and mTOR inhibitor and/or immunosuppressant are independently administered to the subject by a route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous.

In certain embodiments, the pharmaceutical composition is administered to the subject by a route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous.

In certain embodiments, the subject is a mammal. In other embodiments, the mammal is human.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound or composition necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from 1 ng/kg/day and 100 mg/kg/day. In certain embodiments, the invention envisions administration of a dose which results in a concentration of the compound of the present invention from 1 µM and 10 µM in a mammal. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician, having ordinary skill in the art may readily determine and prescribe the effective amount of the pharmaceutical composition required. For example, the physician could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., anti-AD agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475; 6,488,962;

6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In one embodiment, patients require intermittent treatment on a long-term basis upon any recurrence of symptoms and/or infection.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies 20 preferably within a range of circulating concentrations that include the $ED_{50}$ with minimal toxicity. The dosage optionally varies within this range depending upon the dosage form employed and the route of administration utilized.

Combination Therapies

In certain embodiments, the compounds of the invention are useful in the methods of the invention in combination with at least one additional agent useful for treating or preventing a disease or disorder contemplated herein in a mammal in need thereof. This additional agent may comprise compounds identified herein or compounds, e.g., commercially available compounds, known to treat, prevent or reduce the symptoms of a disease or disorder contemplated herein.

In certain embodiments, the at least one additional compound useful for treating or preventing depression comprises citalopram, escitalopram, paroxetine, fluoxetine, sertraline, femoxetine, tranylcypromine, selegiline, isocarboxazid, phenelzine, fluvoxamine, trimipramine, amitriptyline, nortriptyline, desipramine, protriptyline, imipramine, doxepin, clomipramine, maprotiline, bupropion, nefazodone, trazodone, venlafaxine, duloxetine, desvenlafaxine, mirtazapine, and milnacipran.

A synergistic effect may be calculated, for example, using suitable methods such as, for example, the Sigmoid-Emax equation (Holford & Scheiner, 1981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Kits

The invention includes a kit comprising at least one composition of the invention, an applicator, and an instructional material for use thereof.

The instructional material included in the kit comprises instructions for preventing or treating a disease or disorder contemplated within the invention. The instructional material recites the amount of, and frequency with which, at least one composition of the invention should be administered to the mammal. In other embodiments, the kit further comprises at least one additional agent that prevents or treats the disease or disorder contemplated within the invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

The present studies address a longstanding question in the field—whether the antidepressant effects of ketamine depend upon its capacity to stimulate a key protein known as the mechanistic target for rapamycin (mTOR). If that is indeed the case, ketamine's effects should be reduced when mTOR is inhibited. To test this hypothesis, a double-blind placebo-controlled crossover study was conducted under fully randomized conditions, whereby one set of patients was treated with the mTOR inhibitor rapamycin, an FDA approved drug that is currently used to treat certain immune disorders and cancers.

In this design, symptomatic antidepressant-treated patients with major depression who have a history of non-response to at least one prior antidepressant trial were recruited and studied over 3 years. Participants completed two ketamine infusion test days separated by at least two weeks. On each ketamine test day, patients were randomized to take a "loading dose" of rapamycin or placebo 2 hours before receiving an intravenous infusion of ketamine. The primary outcome measure of the study was the severity of depression, as measured by the Montgomery Åsberg Depression Rating Scale (MADRS).

The study showed that administering a single dose of the immunosuppressant rapamycin (also known as sirolimus; an inhibitor of the mechanistic target of rapamycin or mTOR), 2 hours prior to a single ketamine infusion, prolonged the antidepressant effects for at least 2 weeks following treatment. Briefly, in a double-blind crossover balanced design, 23 depressed subjects were randomized to placebo and rapamycin followed by a single infusion of ketamine.

Participants received a single 6 mg oral dose via oral solution of rapamycin or a dose of placebo approximately two hours prior to 0.5 mg/kg of ketamine infused intravenously over 40 minutes. The order of placebo and rapamycin was randomized. The rapamycin dose as well as the placebo solution was given in 2 ounces of orange juice, followed by 4 ounces of water.

Figure 1B:
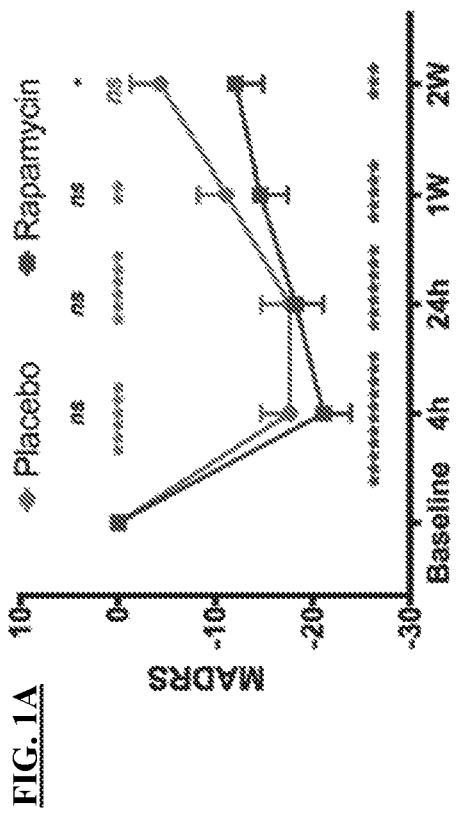
Figure 1C:
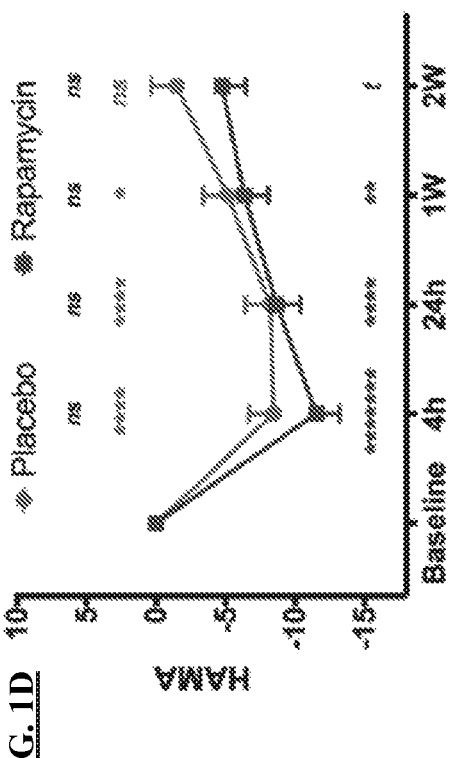
Figure 1D:
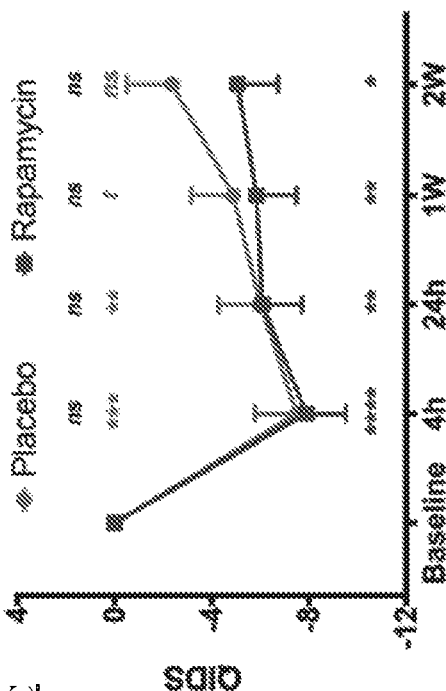

Depression severity was assessed at baseline, and at 4 h, 24 h, 1 week, and 2 weeks post treatment. As shown in FIGS. 1A & 1B, when patients received placebo prior to ketamine, they relapsed within 2 weeks. However, when they received rapamycin prior to ketamine, they continued to report significant reduction in their depressive symptoms as measured by the clinician administered Montgomery-Åsberg Depression Rating Scale (MADRS; primary outcome in this study). FIGS. 1C & 1D show the effects of rapamycin on depression as per the self-report Quick Inventory of Depressive Symptomatology scale (QIDS; FIG. 1C) and on anxiety as per the clinician administered Hamilton Anxiety scale (HAMA; FIG. 1D).

The outcomes of the study provide valuable insights into how and why ketamine works, thus enabling important breakthroughs for its clinical use. Rapamycin was found to enhance the antidepressant effect of ketamine, and thus combinations of ketamine and rapamycin or other potent immunosuppressant approaches can be used to enhance the rapid antidepressant effects of ketamine.

Enumerated Embodiments

The following exemplary embodiments are provided, the numbering of which is not to be construed as designating levels of importance.

Embodiment 1 provides a method of treating or preventing a mood disorder in a human subject, wherein the disease or disorder is treatable or preventable by administering a rapid-acting antidepressant (RAAD) to the subject, the method comprising administering to the subject a therapeutically effective amount of the RAAD and a therapeutically effective amount of a mTOR inhibitor and/or immunosuppressant.

Embodiment 2 provides the method of Embodiment 1, wherein the mood disorder is at least one selected from the group consisting of major depressive disorder (MDD), major depressive episode in bipolar disorder (bipolar depression), persistent depressive disorder (dysthymia), disruptive mood dysregulation disorder, major depressive disorder (including major depressive episode), premenstrual dysphoric disorder, substance/medication-induced depressive disorder, depressive disorder due to another medical condition, other specified depressive disorder, unspecified depressive disorder, anxiety disorder, and posttraumatic stress disorder.

Embodiment 3 provides the method of any of Embodiments 1-2, wherein the RAAD is a NMDA receptor modulator.

Embodiment 4 provides the method of any of Embodiments 1-3, wherein the RAAD and mTOR inhibitor and/or immunosuppressant is co-administered to the subject.

Embodiment 5 provides the method of any of Embodiments 1-4, wherein the mTOR inhibitor and/or immunosuppressant is administered to the subject at least once before the RAAD is administered to the subject.

Embodiment 6 provides the method of any of Embodiments 1-5, wherein the RAAD and mTOR inhibitor and/or immunosuppressant are co-formulated as a pharmaceutical composition.

Embodiment 7 provides the method of any of Embodiments 1-6, wherein the RAAD and mTOR inhibitor and/or immunosuppressant are independently administered to the subject by a route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous.

Embodiment 8 provides the method of any of Embodiments 1-7, wherein the RAAD is at least one selected from the group consisting of: ketamine (also known as RS-ketamine, R/S-ketamine, or (RS)-2-(2-Chlorophenyl)-2-(methylamino)cyclohexanone); R-ketamine (also known as (R)-2-(2-Chlorophenyl)-2-(methylamino)cyclohexanone); S-ketamine (also known as esketamine, or (S)-2-(2-Chlorophenyl)-2-(methylamino) cyclohexanone); hydroxynorketamine (also known as 2-Amino-2-(2-chlorophenyl)-6-hydroxycyclohexan-1-one); rapastinel (also known as (S)—N-[(2S,3R)-1-amino-3-hydroxy-1-oxobutan-2-yl]-1-[(S)-1-((2S,3R)-2-amino-3-hydroxy butanoyl)pyrrolidine-2-carbonyl]pyrrolidine-2-carboxamide); lanicemine (also known as AZD6765, or (1S)-1-phenyl-2-pyridin-2-ylethanamine), D-cycloserine (also known as 4-amino-3-isoxazolidinone); scopolamine (also known as hyoscine or (−)-(S)-3-Hydroxy-2-phenylpropionic acid (1R,2R,4S,5S,7α,9S)-9-methyl-3-oxa-9-azatricyclo[3.3.1.0$^{2,4}$]non-7-yl ester); psilocybin (also known as [3-(2-Dimethylaminoethyl)-1H-indol-4-yl] dihydrogen phosphate); lysergic acid (also known as LSD or 7-Methyl-4,6,6a,7,8,9-hexahydroindolo[4,3-fg]quinoline-9)-carboxylic acid); ayahuasca or any preparations, fractions, or partially or fully purified fractions thereof; DMT (also known as 2-(1H-Indol-3-yl)-N,N-dimethylethanamine); Brexanolone (also known as 1-(3-Hydroxy-10,13-dimethyl-2,3,4,5,6,7,8,9,11, 12, 14, 15, 16, 17-tetradecahydro-1H-cyclopenta[a]phenanthren-17-yl) ethanone; allopregnanolone; 5α-pregnan-3α-ol-20-one; 3α, 5α-tetrahydroprogesterone; 3α, 5α-THP; or Sage-547); 3α-Hydroxy-3β-methyl-21-(4-cyano-1H-pyrazol-1'-yl)-19-nor-5β-pregnan-20-one (also known as 3β-Methyl-21-(4-cyano-1H-pyrazol-1'-yl)-19-norpregnanolone; 3α-Hydroxy-3β-methyl-5β-dihydro-21-(4-cyano-1H-pyrazol-1'-yl)-19-norprogesteroneor Sage-217); (L)-4-Chlorokynurenine (also known as (2S)-2-Amino-4-(2-amino-4-chlorophenyl)-4-oxobutanoic acid or AV-101); NV-5138 (Navitor Pharmaceuticals, Cambridge, MA); D-methadone (also known as (D)-6-(dimethylamino)-4,4-diphenylheptan-3-one); (1R,2R,3R,5R,6R)-2-amino-3-(3,4-dichlorobenzyloxy)-6-fluorobicyclo[3.1.0]hexane-2,6-dicarboxylic acid (also known as MGS-0039); midatofel (also known as CPPene, or (R)-4-[(E)-3-phosphonoprop-2-enyl]piperazine-2-carboxylic acid); selfotel (also known as CGS-19755; or (2S,4R)-4-(phosphonomethyl)piperidine-2-carboxylic acid); apimostinel (also known as NRX-1074; or (2R)-1-[(2S)-1-[(2S,3R)-2-Amino-3-hydroxy butanoyl] pyrrolidine-2-carbonyl]-N-[(2S,3R)-1-amino-3-hydroxy-1-oxobutan-2-yl]-2-benzyl-pyrrolidine-2-carboxamide); basimglurant (also known as RO4917523; or 2-chloro-4-{[1-(4-fluorophenyl)-2,5-dimethyl-1H-imidazol-4-yl]ethynyl}pyridine); decoglurant (also known as RG1578; or 5-({7-(Trifluoromethyl)-5-[4-(trifluoromethyl)phenyl]pyrazolo[1,5-a]pyrimidin-3-yl} ethynyl)-2-pyridinamine); tulrampator (also known as CX-1632; S-47445; or 8-cyclopropyl-3-[2-(3-fluorophenyl) ethyl]-7H-[1,3]oxazino[6,5-g][1,2,3]benzotriazine-4,9-dione); ganaxolone (also known as 1-[(3R,5S,8R,9S,10S,13S,14S,17S)-3-hydroxy-3,10,13-trimethyl-1,2,4,5,6,7,8,9,11,12,14,15,16,17-tetradecahydrocyclopenta[a]phenanthren-17-yl]ethanone); racemic dextromethorphan (also known as racemic (4bS,8aR,9S)-3-Methoxy-11-methyl-6,7,8,8a,9,10-hexahydro-5H-9,4b-(epiminoethano)phenanthrene); dextromethorphan; phencyclidine (also known as 1-(1-phenylcyclohexyl)piperidine); dizocilpine (also known as MK-801 or (5R,10S)-(+)-5-methyl-10,11-dihydro-5H-dibenzo[a,d]cyclohepten-5,10-imine); CERC-301 (also known as MK-0657, or 4-Methylbenzyl (3S,4R)-3-fluoro-4-[(2-pyrimidinylamino)methyl]-1-piperidinecarboxylate); CGP 37849 (also known as (E,2R)-2-amino-4-methyl-5-phosphonopent-3-enoic acid); 1-aminocyclopropanecarboxylic acid; traxoprodil (also known as CP-101,606, or (1S,2S)-1-(4-hydroxyphenyl)-2-(4-hydroxy-4-phenylpiperidino)-1-propanol); Ro 25-6981 (also known as (αR,βS)-α-(4-Hydroxyphenyl)-β-methyl-4-(phenylmethyl)-1-piperidinepropanol); and eliprodil (also known as 1-(4-chlorophenyl)-2-[4-[(4-fluorophenyl)methyl]piperidin-1-yl]ethanol); any salt, solvate, enantiomer, tautomer and geometric isomer thereof, or any mixtures thereof.

Embodiment 9 provides the method of any of Embodiments 1-8, wherein the RAAD is selected from the group consisting of ketamine, S-ketamine, R-ketamine, or any salt, solvate, enantiomer, tautomer and geometric isomer thereof, or any mixtures thereof.

Embodiment 10 provides the method of any of Embodiments 1-9, wherein the RAAD is not selected from the group consisting of ketamine, S-ketamine, R-ketamine, or any salt, solvate, enantiomer, tautomer and geometric isomer thereof, or any mixtures thereof.

Embodiment 11 provides the method of any of Embodiments 1-10, wherein the mTOR inhibitor is at least one selected from the group consisting of BEZ235, rapamycin, everolimus, AZD8055, Temsirolimus, KU-0063794, PI-103, Torkinib, Tacrolimus, Ridaforolimus, INK-128, Voxtalisib, Torin-1, Omipalisib, OSI-027, PF-04691502, Apitolisib, GSK1059615, WYE-354, Gedatolisib, AZD-2014, Torin-2, WYE-125132, BGT226, Palomid-529, PP121, WYE-687, CH5132799, Way-600, ETP-46464, GDC-0349, XL388, and Zotarolimus, or a salt, solvate, enantiomer or diastereoisomer thereof.

Embodiment 12 provides the method of any of Embodiments 1-11, wherein the immunosuppressant is selected from the group consisting of glucocorticoid and calcineurin inhibitor.

Embodiment 13 provides a pharmaceutical composition comprising a RAAD and a mTOR inhibitor and/or immune suppressant, wherein the RAAD and mTOR inhibitor and/or immune suppressant are present in amounts whereby: administration of the pharmaceutical composition to a subject treats in the subject a disease or disorder that is treatable or preventable by the RAAD; and the mTOR inhibitor and/or immune suppressant prolongs at least one biological activity of the RAAD in the subject.

Embodiment 14 provides the pharmaceutical composition of Embodiment 13, which is formulated for administration by a route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous.

Embodiment 15 provides the pharmaceutical composition of any of Embodiments 13-14, which is part of a kit further comprising an applicator, and an instructional material for use thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A pharmaceutical composition comprising:
   a therapeutically effective dose of a N-methyl-D-aspartate (NMDA) receptor modulator selected from the group consisting of racemic ketamine, S-ketamine, R-ketamine, and hydroxynorketamine, or a pharmaceutically acceptable salt, solvate, or tautomer thereof;
   a therapeutically effective dose of rapamycin, or a pharmaceutically acceptable salt, solvate, or tautomer thereof; and
   at least one pharmaceutically acceptable carrier or excipient,
   wherein the therapeutically effective dose of the NMDA receptor modulator and the therapeutically effective dose of the rapamycin are selected such that administration of the pharmaceutical composition to a subject treats or ameliorates a mood disorder selected from the group consisting of major depressive disorder, persistent depressive disorder (dysthymia), disruptive mood dysregulation disorder, premenstrual dysphoric disorder, substance/medication-induced depressive disorder, anxiety disorder, and post-traumatic stress disorder in the subject.

2. The pharmaceutical composition of claim 1, which is formulated for administration by a route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous route.

3. A kit comprising:
   a pharmaceutical composition comprising:
      a therapeutically effective dose of a NMDA receptor modulator selected from the group consisting of racemic ketamine, S-ketamine, R-ketamine, and hydroxynorketamine, or a pharmaceutically acceptable salt, solvate, or tautomer thereof;
      a therapeutically effective dose of rapamycin, or a pharmaceutically acceptable salt, solvate, or tautomer thereof; and
      at least one pharmaceutically acceptable carrier;
      wherein the therapeutically effective dose of the NMDA receptor modulator and the therapeutically effective dose of the rapamycin are selected such that administration of the pharmaceutical composition to a subject treats or ameliorates a mood disorder selected from the group consisting of major depressive disorder, persistent depressive disorder (dysthymia), disruptive mood dysregulation disorder, premenstrual dysphoric disorder, substance/medication-induced depressive disorder, anxiety disorder, and post-traumatic stress disorder in the subject; and
   an instructional material for use thereof.

4. The pharmaceutical composition of claim 1, wherein the NMDA receptor modulator is racemic ketamine, or a pharmaceutically acceptable salt, solvate, or tautomer thereof.

5. The pharmaceutical composition of claim 1, wherein the NMDA receptor modulator is R-ketamine, or a pharmaceutically acceptable salt, solvate, or tautomer thereof.

6. The pharmaceutical composition of claim 1, wherein the NMDA receptor modulator is S-ketamine, or a pharmaceutically acceptable salt, solvate, or tautomer thereof.

7. The pharmaceutical composition of claim 1, wherein the NMDA receptor modulator is present at a dose of 1 mg to 200 mg.

8. The pharmaceutical composition of claim 1, wherein the rapamycin is present at a dose of 0.5 mg to 5 mg.

9. The pharmaceutical composition of claim 1, wherein the NMDA receptor modulator is present at a dose of 5 mg to 100 mg.

10. The pharmaceutical composition of claim 1, wherein the rapamycin is present at a dose of 0.5 mg to 40 mg.

11. The pharmaceutical composition of claim 4, wherein the racemic ketamine is present at a dose of 5 mg to 100 mg.

* * * * *